(12) United States Patent
Ho et al.

(10) Patent No.: US 8,979,804 B2
(45) Date of Patent: Mar. 17, 2015

(54) NEEDLELESS CONNECTOR

(71) Applicant: Pacific Hospital Supply Co., Ltd., Miaoli County (TW)

(72) Inventors: Shih-Chi Ho, Miaoli County (TW); Ming-Chung Chen, Miaoli County (TW)

(73) Assignee: Pacific Hospital Supply Co., Ltd., Miaoli County (TW)

( * ) Notice: Subject to any disclaimer, the term of this patent is extended or adjusted under 35 U.S.C. 154(b) by 116 days.

(21) Appl. No.: 13/726,234

(22) Filed: Dec. 24, 2012

(65) Prior Publication Data

US 2014/0180219 A1 Jun. 26, 2014

(51) Int. Cl.
| | |
|---|---|
| *A61M 5/178* | (2006.01) |
| *A61M 5/00* | (2006.01) |
| *A61M 5/31* | (2006.01) |
| *A61M 25/16* | (2006.01) |
| *A61M 25/18* | (2006.01) |
| *A61M 39/00* | (2006.01) |
| *A61M 39/10* | (2006.01) |
| *A61M 39/24* | (2006.01) |
| *A61M 39/26* | (2006.01) |

(52) U.S. Cl.
CPC ....... *A61M 39/10* (2013.01); *A61M 2039/2486* (2013.01); *A61M 2039/263* (2013.01)
USPC ....... 604/167.02; 604/241; 604/533

(58) Field of Classification Search
USPC ....... 604/167.01–167.04, 236–237, 604/240–241, 256, 537, 539
See application file for complete search history.

(56) References Cited

U.S. PATENT DOCUMENTS

| 5,738,144 A * | 4/1998 | Rogers ..................... 137/614.03 |
| 5,820,601 A * | 10/1998 | Mayer ..................... 604/167.02 |
| 7,975,722 B2 * | 7/2011 | Kiehne ..................... 137/854 |

\* cited by examiner

*Primary Examiner* — Rebecca E Eisenberg
(74) *Attorney, Agent, or Firm* — Chun-Ming Shih; HDLS IPR Services

(57) ABSTRACT

A needleless connector includes a hollow connector, a spring, and a switch assembly. The inner perimeter of the hollow connector forms a first annular wall and a second annular wall. The spring is disposed in the hollow connector. The switch assembly has a stop member and a guide tube connected to the stop member, the stop member being pressed between the annular block and the spring, the guide tube being disposed in the hollow connector, the external perimeter of the stop member forming a first annular portion against the first annular wall and a second annular portion against the second annular wall, a groove being disposed between the first annular portion and the second annular portion of the stop member, the groove being connected to the guide tube. Thus, the integral structure stability and good closing performance are achieved such that the outside air cannot leak into the connector structure.

10 Claims, 6 Drawing Sheets

NEEDLELESS CONNECTOR

BACKGROUND OF THE INVENTION

1. Field of the Invention

The present invention relates to a medial device for blood transfusion or liquid medicine delivery, more particularly to a needleless connector.

2. Description of Prior Art

A conventional syringe is commonly used as the device for medicine injection. The needle of the syringe is a sharp structure and therefore, it is possible for the medical personnel to suffer needlestick injury when they use the syringe carelessly. If the needle is contaminated, the medical personnel will be exposed to infection. As a result, the used needles are not allowed to be arbitrarily discarded and they need to be recycled and treated professionally to reduce the possibilities of personnel's infection and environmental contamination in order to improve the safety of operation, which in contrast increases the medical cost. Therefore, needleless connectors are currently available in the market and are used for medical injection with needleless syringes. This type of device has the features of low risk and reuse, and could reduce the cost incurred by considerable effort of recycling.

The above-mentioned needleless connector, as shown in U.S. Pat. No. 7,713,250 having the title "Needleless luer access connector", has a housing and a septum. The housing has a channel disposed therein. The septum is disposed in the housing and blocks in front of the channel to seal the channel. The septum is a flexible member and has a slit disposed at the center thereof. In this way, the needleless syringe can be inserted into the septum through the slit to deform the septum to open the channel, and then the liquid in the needleless syringe can flow into the patient.

However, the structure of the needleless luer access connector disclosed in U.S. Pat. No. 7,713,250 is not stable. The reason is given below in detail. The open-close switching of the channel is controlled by the open-close switching of the slit. If the slit suffers elastic fatigue after long service, it will close incompletely and reduce efficiency of closing. Consequently, after injection and then syringe withdrawal, the blood and liquid medicine could flow reversely into the connector due to negative pressure and leak out from the slit, causing the medical personnel and environment to be contaminated.

In view of this, the inventor pays special attention to research with the application of related theory and tries to overcome the above disadvantages regarding the above prior art, which is the goal of the present invention.

SUMMARY OF THE INVENTION

An objective of the present invention is to provide a needleless connector, which uses a spring to automatically replace a stop member when an externally exerted force disappears and uses a first annular portion and a second annular portion to block a channel to enhance the integral structure stability and achieve good closing performance of the needleless connector such that the outside air can not leak into the connector structure.

In order to achieve the above objective the present invention provides a needleless connector comprising a hollow connector having a first channel and a second channel connected to each other at both ends, the perimeter of the first channel extending inward to have an annular block, the inner perimeter of the annular block forming a first annular wall, a second annular wall being formed between the annular block and the second channel in the first channel; a spring disposed in the first channel; and a switch assembly having a stop member and a guide tube connected to the stop member, the stop member being pressed between the annular block and the spring, the guide tube being disposed in the second channel, the external perimeter of the stop member forming a first annular portion against the first annular wall and a second annular portion against the second annular wall, a groove being disposed between the first annular portion and the second annular portion of the stop member, the groove being connected to the guide tube.

Besides, the present invention has the following effects:

First, the spring which could suffer elastic fatigue caused by force exertion only carries out the function of automatically replacing the stop member during which the first annular portion and the second annular portion of the stop member block the channel to fulfill the function of closing the needleless connector to prevent the outside air from leaking into the connector or to prevent the liquid medicine and blood in the patient from flowing reversely. Therefore, even though the spring suffers elastic fatigue after long service, the closing capability of the stop member is still not affected. As a result, the needleless connector of the present invention can have excellent structure stability and closing capability.

Second, the needle of prior art is not required and instead the mutual connection of the needleless injector and the needleless connector is used during blood transfusion or liquid medicine delivery. That further avoids the needlestick injury, replacement and recycling of needles to reduce medical costs.

Third, during the sliding of the stop member in the first channel, the second annular portion formed by the external perimeter of the stop member has been disposed against the second annular wall to prevent the liquid from leaking elsewhere through the gaps between the stop member and the second annular wall. In this way, the liquid is ensured to flow in the groove to achieve good liquid-guiding stability of the needleless connector of the present invention.

Fourth, the stop member comprises the plug and two O-rings disposed around the plug. The plug is made of rigid materials and the O-rings are made of materials such as rubber and silicone. The plug forms the first annular portion and the second annular portion corresponding to the two O-rings. Thus, the present invention uses the component which is produced simply and handily to easily assemble the stop member of a stable structure, further reducing the manufacturing cost of the needleless connector.

Fifth, the intake surface is formed on the surface of the stop member contacting the injection needle. The perimeter of the intake surface has an end edge and at lease one guide groove is disposed at the end edge to assist the liquid in flowing into the first channel through the guide groove. That prevents the liquid from being blocked by the surface of the stop member and thus eases the problem of reverse flow of the liquid.

DETAILED DESCRIPTION OF THE INVENTION

Figure 1:
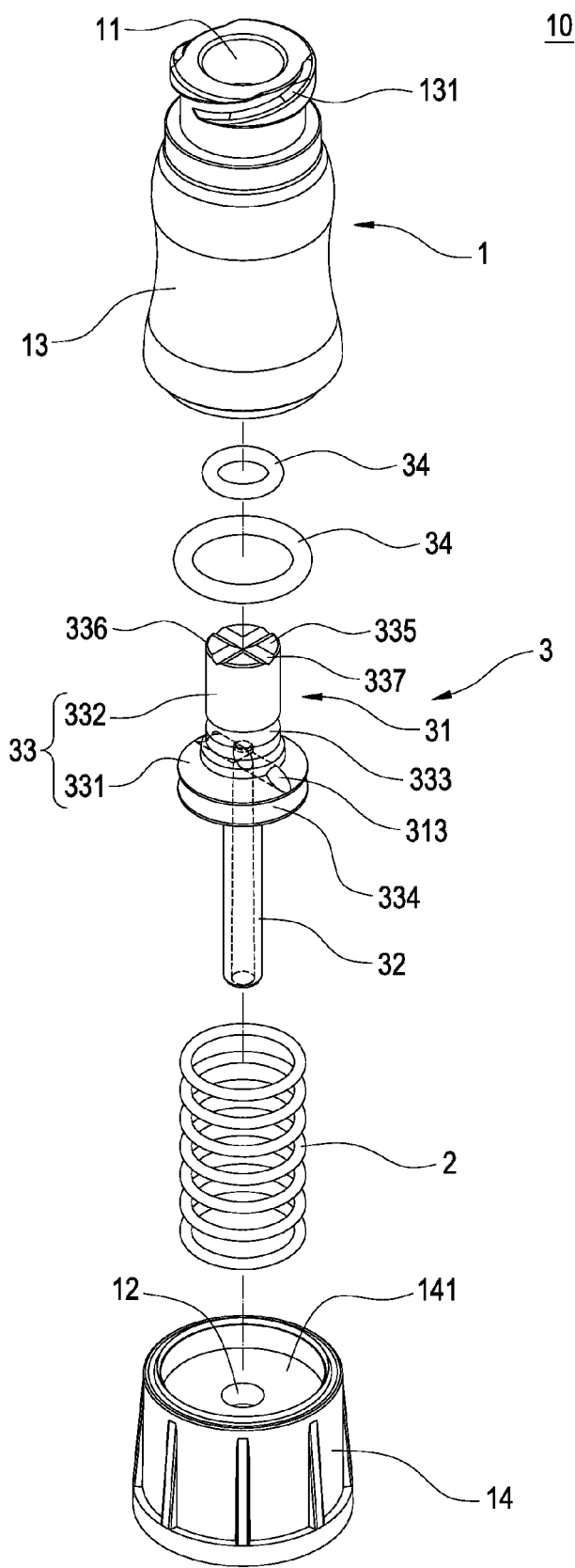
FIG. 1 is an exploded perspective view of the needleless connector of the present invention.
Figure 2:
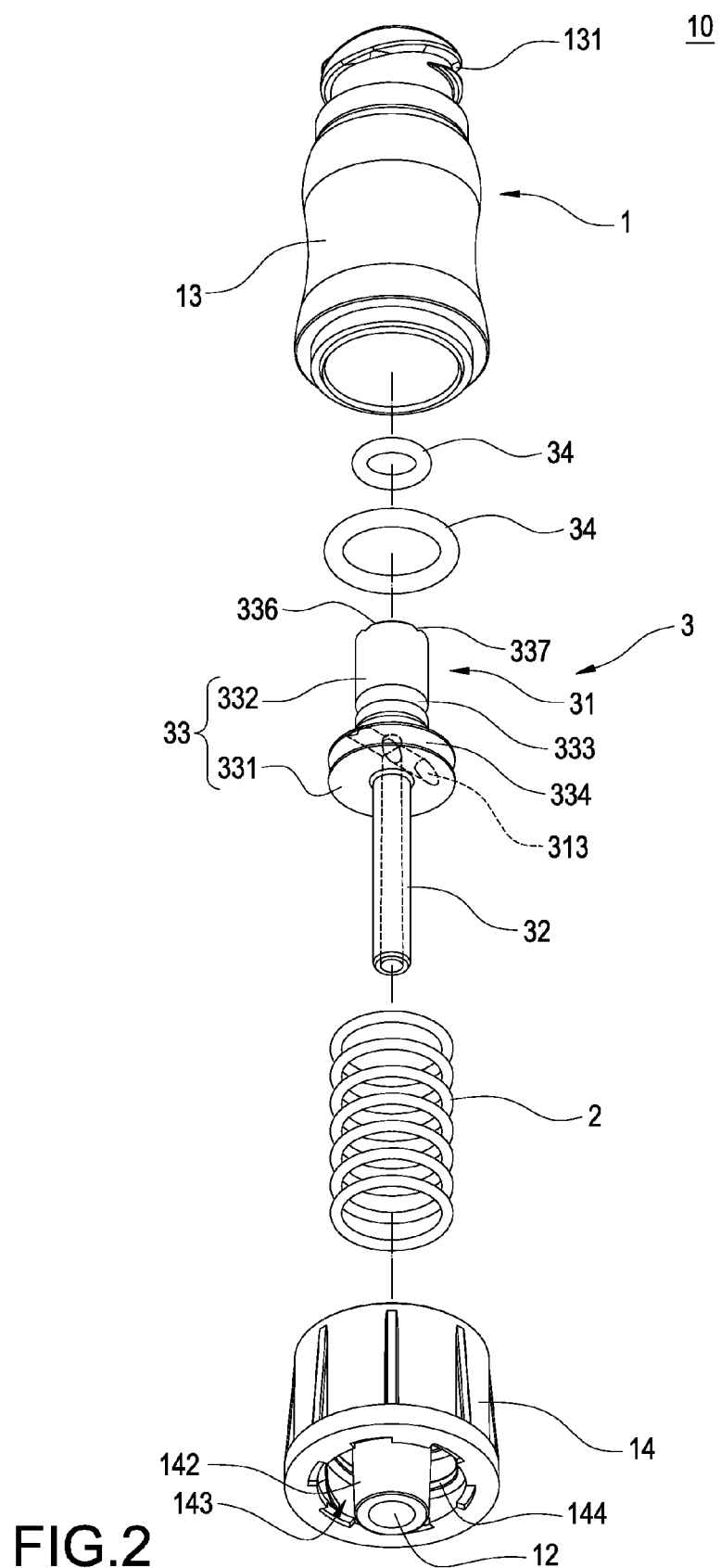
FIG. 2 is an exploded perspective view of the needleless connector of the present invention from another view.
Figure 3:
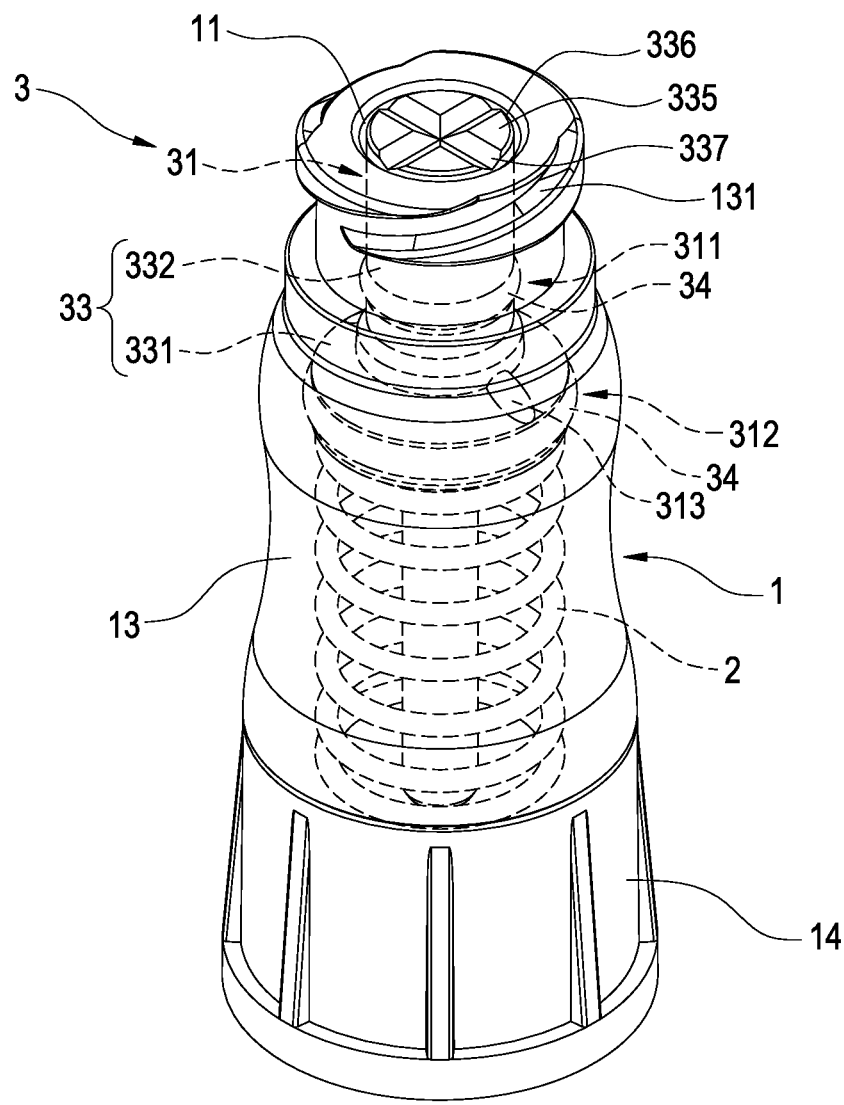
FIG. 3 is an assembled schematic view of the needleless connector of the present invention.
Figure 4:
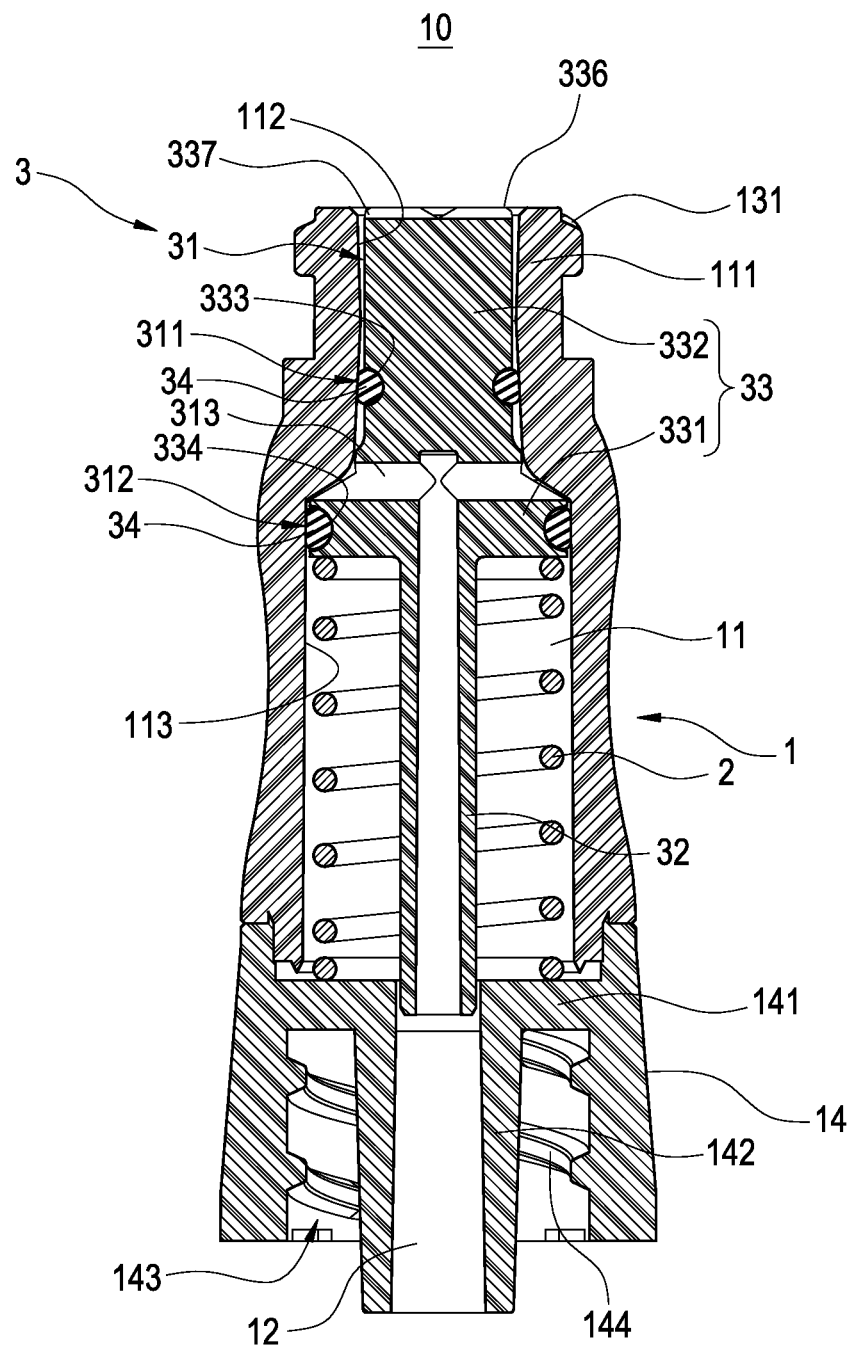
FIG. 4 is a cross sectional view of the needleless connector of the present invention.

The detailed description and technology of the present invention will be described as follows with figures and description. However, the accompanying figures are provided only for explanation, but not for limiting the present invention.

Please refer to FIGS. 1-4, in which the present invention is to provide a needleless connector 10 mainly comprising a hollow connector 1, a spring 2, and a switch assembly 3.

The hollow connector 1 has a first channel 11 and a second channel 12 connected to each other at both ends. The perimeter of the first channel 11 extends inward to have an annular block 111. The inner perimeter of the annular block 111 forms a first annular wall 112. A second annular wall 113 is formed between the annular block 111 and the second channel 12 in the first channel 11. The size of the perimeter of the first annular wall 112 is smaller than that of the second annular wall 113.

The detailed description is given below. The hollow connector 1 comprises a first hollow body 13 and a second hollow body 14 assembled to each other. The first channel 11 is formed in the first hollow body 13. The second hollow body 14 extends from the internal perimeter thereof to form a separation plate 141 and extends from the separation plate 141 away from the first hollow body 13 to form a hollow tube 142. The second channel 12 is formed in the hollow tube 142.

Besides, an external thread 131 is disposed at the end portion of the first hollow body 13 away from the second hollow body 14. A recessed portion 143 is formed between the separation plate 141 and the hollow tube 142 in the second hollow body 14. An internal thread 144 is disposed at the outer perimeter of the recessed portion 143.

The spring 2 is disposed in the first channel 11. The spring 2 can, but not limited to, be a helical spring.

The switch assembly 3 has a stop member 31 and a guide tube 32 connected to the stop member 31. The stop member 31 is pressed between the annular block 111 and the spring 2. The guide tube 32 is disposed in the second channel 12. The external perimeter of the stop member 31 forms a first annular portion 311 against the first annular wall 112 and a second annular portion 312 against the second annular wall 113. A groove 313 is disposed between the first annular portion 311 and the second annular portion 312 of the stop member 31. The groove 313 is connected to the guide tube 32.

The stop member 31 comprises a plug 33 and two O-rings 34 disposed around the plug 33. The plug 33 is made of rigid materials such as plastic and the O-rings 34 are made of materials such as rubber and silicone. The plug 33 extends to have the guide tube 32, and to form the first annular portion 311 and the second annular portion 312 corresponding to the two O-rings 34, and the plug 33 has the groove 313.

The plug 33 has a shoulder 331 and a head 332 extending from the shoulder 331 away from the guide tube 32, the size of the perimeter of the shoulder 331 is larger than that of the head 332, a first annular groove 333 is disposed around the perimeter of the head 332, a second annular groove 334 is disposed around the perimeter of the shoulder 331, and the two O-rings 34 are positioned in the first annular groove 333 and the second annular groove 334, respectively.

In addition, an intake surface 335 is formed on one end of the plug 33 away from the guide tube 32. The perimeter of the intake surface 335 has an end edge 336. One or a plurality of guide grooves 337 is disposed at the end edge 336.

Furthermore, one end of the spring 2 is placed against the plug 33 and the other end of the spring 2 is placed against the separation plate 141. In this way, the spring 2 is disposed in the first channel 11 and exerts a force on the plug 33 toward the annular block 111.

The assembly of the needleless connector 10 of the present invention is explained below. The hollow connector 1 has a first channel 11 and a second channel 12 connected to each other at both ends, the perimeter of the first channel 11 extending inward to have an annular block 111, the inner perimeter of the annular block 111 forming a first annular wall 112, a second annular wall 113 being formed between the annular block 111 and the second channel 12 in the first channel 11; the spring 2 is disposed in the first channel 11; the switch assembly 3 has a stop member 31 and a guide tube 32 connected to the stop member 31, the stop member 31 being pressed between the annular block 111 and the spring 2, the guide tube 32 being disposed in the second channel 12, the external perimeter of the stop member 31 forming a first annular portion 311 against the first annular wall 112 and a second annular portion 312 against the second annular wall 113, a groove 313 being disposed between the first annular portion 311 and the second annular portion 312 of the stop member 31, the groove 313 being connected to the guide tube 32. In this way, the spring 2 which could suffer elastic fatigue caused by force exertion only carries out the function of automatically replacing the stop member 31 during which the first annular portion 311 and the second annular portion 312 of the stop member 31 block the channel to further fulfill the function of closing the needleless connector 10 to prevent the outside air from leaking into the connector or to prevent the liquid medicine and blood in the patient from flowing reversely. Therefore, even though the spring 2 suffers elastic fatigue after long service, the closing capability of the stop member 31 is still not affected. As a result, the needleless connector 10 of the present invention can have excellent structure stability and closing capability.

Figure 5:
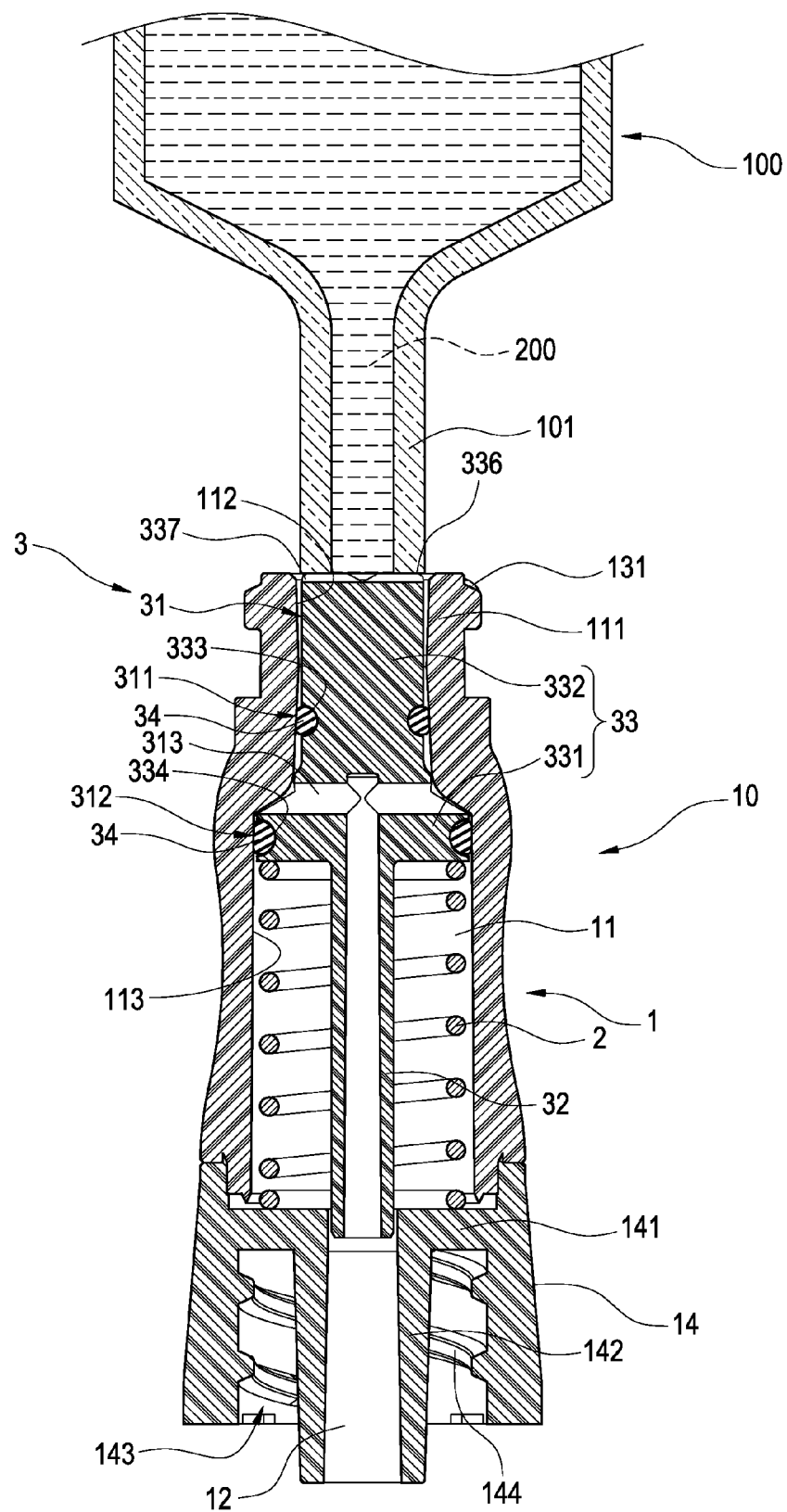
FIG. 5 is a schematic view of the needleless connector of the present invention in a state of use.
Figure 6:
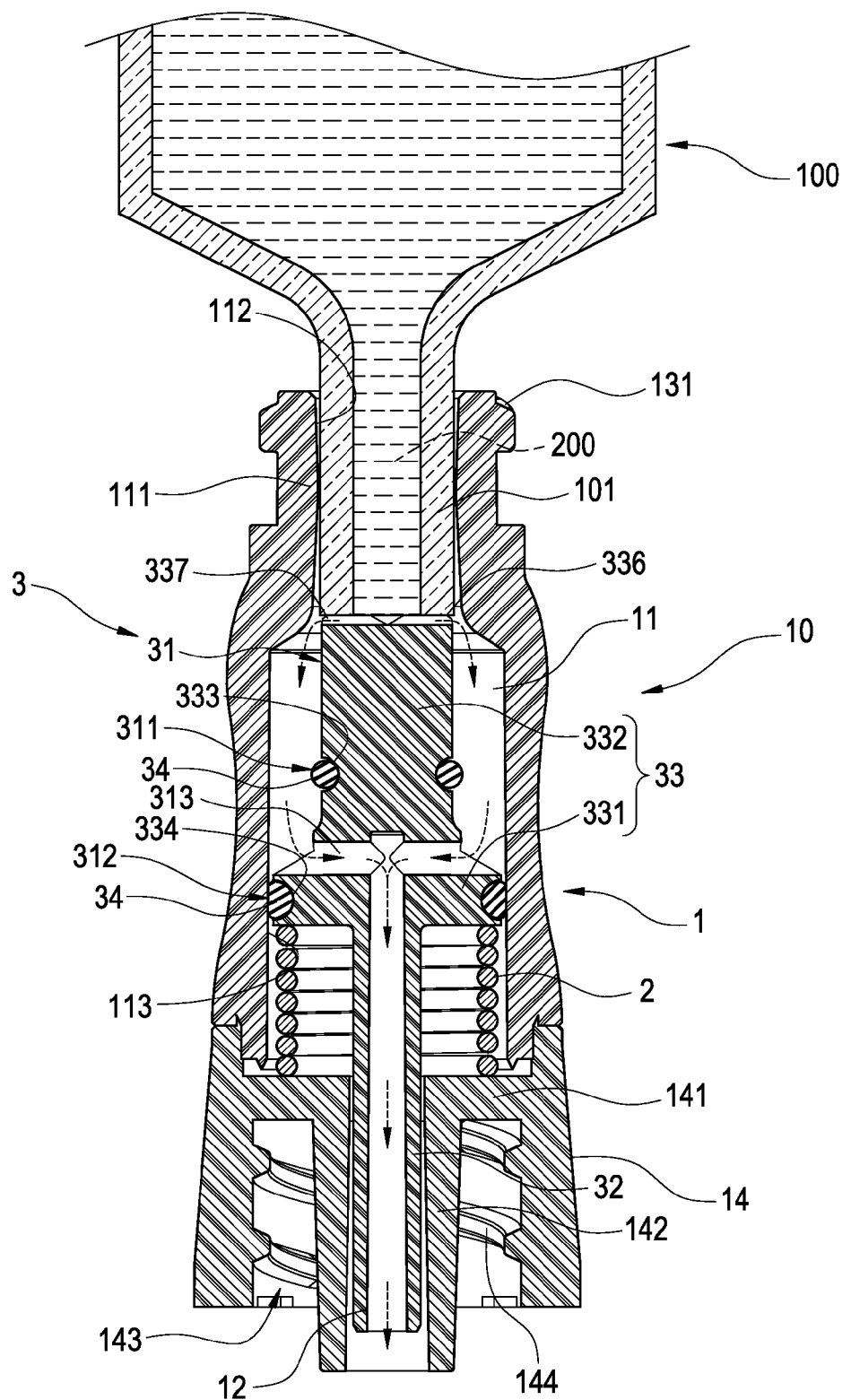
FIG. 6 is a schematic view of the needleless connector of the present invention in another state of use.

Please refer to FIGS. 5 and 6, which show the needleless connector 10 of the present invention in states of use, wherein the injection needle 101 of the needleless syringe 100 is inserted through the first channel 11 of the hollow connector 1. The injection needle 101 exerts a force to compress and deform the spring 2, causing the stop member 31 to move inward; meanwhile, the first annular portion 311 originally located on the first annular wall 112 moves to the second annular wall 113. Since the size of the perimeter of the first annular wall 112 is smaller than that of the second annular wall 113, the first annular portion 311 loses its closing capability. Consequently, the liquid 200 in the needleless syringe 100 flows into the first channel 11 through the intake surface 335 and then into the guide tube 32 and the second channel 12 through the groove 313, and finally into the patient to take effect. In this way, the needle of prior art is not required and instead the mutual connection of the needleless injector 100 and the needleless connector 10 is used during blood transfusion or liquid medicine delivery. That further avoids the needlestick injury, replacement and recycling of needles to reduce medical costs.

In addition, during the sliding of the stop member 31 in the first channel 11, the second annular portion 312 formed by the external perimeter of the stop member 31 has been disposed against the second annular wall 113 to prevent the liquid 200 from leaking elsewhere through the gaps between the stop member 31 and the second annular wall 31. In this way, the liquid 200 is ensured to flow in the groove 313 to achieve good liquid-guiding stability of the needleless connector 10 of the present invention.

Moreover, the stop member 31 comprises the plug 33 and two O-rings 34 disposed around the plug 33. The plug 33 is made of rigid materials and the O-rings 34 are made of materials such as rubber and silicone. The plug 33 forms the first annular portion 311 and the second annular portion 312 corresponding to the two O-rings 34. Thus, the present invention uses the component which is produced simply and handily to easily assemble the stop member 31 of a stable structure, further reducing the manufacturing cost of the needleless connector 10.

Also, the intake surface 335 is formed on the surface of the stop member 31 contacting the injection needle 101. The perimeter of the intake surface 335 has an end edge 336 and at lease one guide groove 337 is disposed at the end edge 336 to assist the liquid in flowing into the first channel 11 through the guide groove 337. That prevents the liquid 200 from being blocked by the surface of the stop member 31 and thus eases the problem of reverse flow of the liquid 200.

In summary, the needleless connector of the present invention indeed achieves the expected objective and overcome the disadvantages of prior art. Therefore, the present invention is useful, novel and non-obvious. Please examine the application carefully and grant it a patent for protecting the rights of the inventor.

What is claimed is:

1. A needleless connector (10), comprising:
   a hollow connector (1) having a first channel (11) and a second channel (12) connected to each other at both ends, a separation plate (141) being formed between the first channel (11) and the second channel (12), the perimeter of the first channel (11) extending inward to have an annular block (111), the inner perimeter of the annular block (111) forming a first annular wall (112), a second annular wall (113) being formed between the annular block (111) and the second channel (12) in the first channel (11);
   a spring (2) disposed in the first channel (11); and
   a switch assembly (3) having a stop member (31) and a guide tube (32) connected to the stop member (31), the stop member (31) comprising a plug (33) and two O-rings (34) disposed around the plug (33), a guide tube (32) extending from the plug (33), the stop member (31) being pressed between the annular block (111) and the spring (2), the guide tube (32) being disposed in the second channel (12), the external perimeter of the stop member (31) forming a first annular portion (311) and a second annular portion (312), one of the two O-rings being disposed in the first annular portion (311) and directly slidably against the first annular wall (112), the other one of the two O-rings being disposed in the second annular portion (312) and directly slidably against the second annular wall (113), a groove (313) being disposed between the first annular portion (311) and the second annular portion (312) of the stop member (31), the groove (313) being connected to the guide tube (32), wherein the spring (2) is disposed between the stop member (31) and the separation plate (141) in the first channel (11); and
   wherein the first annular portion (311) moves into a space between the annular block (111) and the second channel (12) and the O-ring disposed in the first annular portion (311) does not directly contact the first annular wall (112) when the stop member (31) is pushed toward the second channel (12) until a liquid is able to flow into the guide tube (32).

2. The needleless connector (10) according to claim 1, wherein the size of the perimeter of the first annular wall (112) is smaller than that of the second annular wall (113).

3. The needleless connector (10) according to claim 1, wherein the plug (33) extends to have the guide tube (32) and to form the first annular portion (311) and the second annular portion (312) corresponding to the two O-rings (34), and the plug (33) has the groove (313).

4. The needleless connector (10) according to claim 3, wherein the plug (33) has a shoulder (331) and a head (332) extending from the shoulder (331) away from the guide tube (32), the size of the perimeter of the shoulder (331) is larger than that of the head (332), a first annular groove (333) is disposed around the perimeter of the head (332), a second annular groove (334) is disposed around the perimeter of the shoulder (331), and the two O-rings (34) are positioned in the first annular groove (333) and the second annular groove (334), respectively.

5. The needleless connector (10) according to claim 3, wherein an intake surface (335) is formed on one end of the plug (33) away from the guide tube (32), the perimeter of the intake surface (335) has an end edge (336), and at least one guide groove (337) is disposed at the end edge (336).

6. The needleless connector (10) according to claim 3, wherein one end of the spring (2) is placed against the plug (33).

7. The needleless connector (10) according to claim 1, wherein the hollow connector (1) comprises a first hollow body (13) and a second hollow body (14) assembled to each other, the first channel (11) is formed in the first hollow body (13), the second hollow body (14) extends from the internal perimeter thereof to form the separation plate (141) and extends from the separation plate (141) away from the first hollow body (13) to form a hollow tube (142), and the second channel (12) is formed in the hollow tube (142).

8. The needleless connector (10) according to claim 7, wherein an external thread (131) is disposed at the end portion of the first hollow body (13) away from the second hollow body (14), a recessed portion (143) is formed between the separation plate (141) and the hollow tube (142) in the second hollow body (14), and an internal thread (144) is disposed at the outer perimeter of the recessed portion (143).

9. The needleless connector (10) according to claim 7, wherein one end of the spring (2) is placed against the separation plate (141).

10. The needleless connector (10) according to claim 1, wherein the spring (2) is a helical spring.

* * * * *